United States Patent [19]

Barabas

[11] Patent Number: 4,684,698

[45] Date of Patent: Aug. 4, 1987

[54] WATER SOLUBLE MULTICOMPLEX OF CHLOROTHIAZIDE, FUROSEMIDE AND POLY(N-VINYL-2-PYRROLIDONE)

[75] Inventor: Eugene S. Barabas, Watchung, N.J.

[73] Assignee: GAF Corporation, Wayne, N.J.

[21] Appl. No.: 858,978

[22] Filed: May 2, 1986

[51] Int. Cl.⁴ .............................................. C08F 8/34
[52] U.S. Cl. .................................. 525/326.9; 424/78; 424/80; 525/348; 525/349
[58] Field of Search .................. 525/326.9; 424/78, 80

[56] References Cited

U.S. PATENT DOCUMENTS

| | | | |
|---|---|---|---|
| 3,673,163 | 6/1972 | Walking | 424/80 |
| 3,923,974 | 12/1975 | Andrews et al. | 424/80 |
| 3,957,972 | 5/1976 | Weber | 424/80 |
| 3,985,540 | 10/1976 | Fein et al. | 525/326.9 |
| 4,213,963 | 7/1980 | Mesens et al. | 424/80 |
| 4,228,152 | 10/1980 | Ferruti et al. | 525/326.9 |
| 4,291,015 | 9/1981 | Keith et al. | 424/80 |
| 4,292,302 | 9/1981 | Keith et al. | 424/80 |
| 4,344,934 | 8/1982 | Martin et al. | 424/78 |
| 4,472,372 | 9/1984 | Keith et al. | 424/78 |
| 4,542,025 | 9/1985 | Tice et al. | 424/78 |

Primary Examiner—Joseph L. Schofer
Assistant Examiner—Bernard Lipman
Attorney, Agent, or Firm—Marilyn J. Maue; Joshua J. Ward

[57] ABSTRACT

The invention relates to the novel water soluble chlorothiazide-furosemide-poly(N-vinyl-2-pyrrolidone) complex which is derived from the reaction of these components in alkaline media and to the process for the preparation of said complex.

7 Claims, No Drawings

WATER SOLUBLE MULTICOMPLEX OF CHLOROTHIAZIDE, FUROSEMIDE AND POLY(N-VINYL-2-PYRROLIDONE)

Chlorothiazide(6-chloro-7-sulfamyl-1,2,4-benzo-thiadiazine-1,1-dioxide) is a known antihypertensive and diuretic drug which is also used to treat congestive heart failure in animals. Furosemide(4-chloro-N-furfuryl-5-sulfamoyl anthranilic acid) is also a well known diuretic. However, administration of these compounds in solution is complicated by their water-insolubility. Because of their applications in pharmaceutical areas, it is important that no solvent having toxic or other deleterious side effects be employed for solubilization of these compounds in medicinal uses.

Accordingly, it is an object of the present invention to provide a highly water soluble form of chlorothiazide and furosemide with no objectionable side effects.

Another object of this invention is to provide a commercially feasible process for the production of chlorothiazide and furosemide in highly water soluble form.

Another object is to provide a chlorothiazide in a water soluble form having fortified diuretic properties.

These and other objects of the invention will become apparent from the following description and disclosure.

According to this invention there is provided a multicomplexed water soluble product derived from the reaction between poly(N-vinyl-2-pyrrolidone, chlorothiazide and furosemide. This product is a true complex containing repeating units of the complexed furosemide/vinyl pyrrolidone moiety and the complexed chlorothiazide/vinyl pyrrolidone moiety structures.

The complexed product of this invention may also contain non-complexed vinylpyrrolidone moiety sites of the general formula:

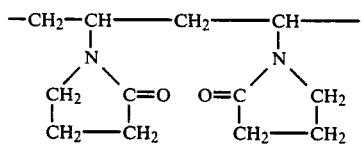

It is most probable that the bonding between the polymer and the drugs takes place through hydrophobic bonding in which the aromatic moieties of the drug compounds and the hydrocarbon chain of the poly(vinyl pyrrolidone) are responsible for the complexing interaction. The hydrophobic bonding force will bring the drug molecules and the polymer chain in close contact where short range dispersion forces become operative and contribute to the stabilization of the complex. While complexation through hydrogen bonding between the carbonyl group of the pyrrolidone ring and the proton present in the donors of the respective imino drugs cannot be entirely excluded, the probability of such effect is small, under the conditions of the reaction and the initial formation of a salt. However, once the salt is destroyed, hydrogen bonding becomes more possible.

The scope of this invention is not to be restricted by theoretical considerations with respect to the nature of the complex bonding since it will be recognized that the ability of the compound to be complexed and solubilized by poly(vinyl pyrrolidone) depends to a great extent upon the chemical, physical and morphological characteristics of the compound, the hydrophilic-hydrophobic ratio of its structural elements, the nature and relative position of its substituents, the bulkiness of the molecule in general and the substituents in particular. Small differences in any of the above factors may significantly alter the solubilizing capability. While the complexability of the compound with poly(vinyl pyrrolidone) may be predicted to some extent, on the chemical character of its substituents, its solubility cannot be predicted on structural similarities alone. Instead a combination of aforesaid factors interacting between the compound to be complexed and the polymer must be considered. Thus, each compound must be viewed and tested individually for a determination of its solubility. To illustrate the above discussion, a compound having solubility parameters similar to both chlorothiazide and furosemide, including good solubility in alkali hydroxides, is represented by chlorzoxazone, i.e.

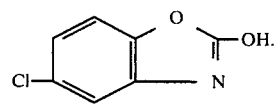

This compound has a phenolic-type hydroxyl substituent, which complexes readily with poly(vinyl pyrrolidone). Nevertheless, the coprecipitate of this compound with poly(vinyl pyrrolidone) was found to be insoluble in water, while the coprecipitate of chlorothiazide and furosemide showed good water solubility.

The complexed units in the polymer may occur in block, random or alternating distribution. In any case, the resulting product contains at least 8 wt. % complexed units preferably at least 12 wt. % complexed units of furosemide and chlorothiazide in the product, and in amounts sufficient to retain properties associated with the chlorothiazide fortified with furosemide. The complexed state of chlorothiazide and furosemide in the product, which compounds can be incorporated in a ratio of from about 1:99 to about 99:1, has been established by experiment showing that even at gradual dilution from 2% to 0.01% in water, no free chlorothiazide or furosemide precipitates from the aqueous solution. If the chlorothiazide and furosemide components had not complexed, they would have precipitated out of solution within the range of dilution. A complex water solubility of at least 15% is desired and water solubility as high as 25% has been achieved. That the material remains in solution at high dilution, significantly above the solubility limit of uncomplexed chlorothiazide, i.e. 0.05% at room temperature, is indeed unexpected.

While the complexes of the invention are stable under normal conditions, they are subject to in vivo hydrolytic forces and other physical chemical effects which lead to slow dissociation. Therefore these complexes can function as slow release systems suitable for the sustained delivery of the drug portion of the complex in medical and veterinarial applications.

The product of this invention preferably contains complexed and un-complexed N-vinyl-2-pyrrolidone units derived from poly(N-vinyl-2-pyrrolidone) having a K value between 12 and 30; although polymers from oligomers to K-90 may also be employed in certain cases. Polymers of K-100 or more, because of their high solution viscosity, may limit the amount of drug molecules which they can bring into solution in complexed form.

Chlorothiazide and furosemide in the complexed state of this invention are generally present in an amount of from about 10 wt. % to about 30 wt. % and exhibit at least a 50 fold increase in water solubility over the uncomplexed compounds. The preferred amount of chlorothiazide and furosemide in the complexed product herein disclosed is between about 12 wt. % and about 20 wt. % and the preferred weight ratio of chlorothiazide to furosemide is between about 45:55 and about 60:40.

The multicomplex of this invention is prepared by a relatively simple and direct process which involves separately dissolving the drugs and the N-vinyl-2-pyrrolidone in an aqueous alkali metal hydroxide solutions, e.g. a 1.8–5% sodium hydroxide or potassium hydroxide solutions to provide solutions wherein the vinylpyrrolidone and the drug reactants are present in between about 5 and about 25 weight % concentration, preferably between about 8% and about 15% by weight concentration of active components.

The poly(N-vinyl-2-pyrrolidone) reactant in the complexing reaction is one having the formula

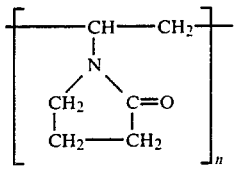

wherein n is an integer having a value of from 5 to 3,500.

The solutions of reactant species are then combined in a weight ratio of poly(N-vinyl-2-pyrrolidone) to mixture of chlorothiazide and furosemide of between about 1:1 and about 10:1, preferably in a ratio of 4–7:1, and thoroughly mixed under atmospheric pressure, or superatmospheric pressure up to 50 psig, at a temperature above 3° C. and below the boiling point of the hydroxide solution which includes a range of between about 4° C. and about 100° C., preferably between about 10° C. and about 40° C. The mixture, which is at a pH of between about 7.5 and about 10, preferably between about 8 and about 9, is agitated under these conditions for a period of from about 5 minutes to about 3 hours, more often between about 10 and about 30 minutes to effect the complexing reaction which produces the alkali salt of the chlorothiazide and fursemide moieties in the complexed compound.

After completion of the reaction, or complexing to the degree desired, the resulting liquid mixture comprising the alkali metal salt moieties of the complex and aqueous alkali metal hydroxide solvent, is treated to remove solvent by any conventional means, such as rotary evaporation or freeze drying. Evaporation is conducted in vacuo, e.g. under a pressure of from about 2 to about 40 mm Hg, preferably not more than 25 mm Hg. The complexed salt liquid is recovered and dried at a temperature between about 45° C. and about 100° C., preferably between about 50° C. and about 65° C. in vacuo for a period of 1 to 24 hours to produce a solid salt complex.

The dried complex is then mixed with water and the pH is adjusted to between about 3.5 and about 7, preferably to between about 5 and about 6.3 with a mineral acid, preferably HCl in a 1.8–5% aqueous solution, to convert the complexed alkali metal salt of the sulfamyl group to a sulfamyl radical and the metal carboxylate group to a carboxyl radical so as to produce the complexed product of the invention.

The resulting chlorothiazide and furosemide in this complexed form is stable and is found to have a water solubility increased from about 0.05% to at least 15% or more at room temperature.

Having thus generally described the present invention, reference is now had to the following examples which illustrate preferred embodiments but which are not to be construed as limiting to the scope of the invention as more broadly set forth hereinabove and in the appended claims.

EXAMPLE 1

Poly(N-vinyl-2-pyrrolidone), K-30 (12.5 grams) was dissolved in 112.5 grams of a 2% aqueous sodium hydroxide solution and poured into a dropping funnel. Chlorothiazide (1.25 grams) dissolved in 11.25 grams of 2% aqueous sodium hydroxide solution and 1.25 grams of furosemide in 11.25 grams of 2% aqueous hydroxide solution were poured into separate dropping funnels. The solutions from each dropping funnel were gradually added to a 500 ml glass flask over a period of 15 minutes during which period they were thoroughly mixed at room temperature at atmospheric conditions. The contents of the flask was then subjected to rotary evaporation under 21 mm Hg vacuum at 80° C. to remove the water. The dried material which is the sodium salt of the complex was ground in a mortar to a particle fineness passing a 100 mesh screen.

In a screwcap jar, 2 grams of the above salt complex was agitated on a horizontal shaker at room temperature with 20 grams of distilled water, corresponding to a 1.6% solution of the chlorothiazide and furosemide. After about 0.5 hour a clear solution was obtained and the pH was adjusted to 5.5 with a small amount of concentrated hydrochloric acid solution. The complexed chlorothiazide and furosemide remained in solution at the acid pH.

An additional 2 grams of the salt complex was added to the clear liquid, thus raising the concentration of chlorothiazide and furosemide to 3.2%. The pH was again adjusted to 6 without the appearance of haze. The step of additional 2 gram additions with adjustment of the pH to the acid side was repeated 5 times until a total of 14 grams of the polymer-chlorothiazide-furosemide complex was reached, corresponding to 10.5% solution of chlorothiazide and furosemide in water. After adjusting the pH to 6.2, the solution remained clear and its clarity did not diminish on standing for 7 days.

As a control, 1 gram of chlorothiazide in 90 grams of distilled water was introduced into a screwcap jar and the pH adjusted to 6 with a buffer solution. Water was added to bring concentration of chlorothiazide to 1% and the mixture was shaken at room temperature for 24 hours after which the solubility of chlorothiazide was found to be 0.05%.

The solubility test for chlorothiazide was repeated except that furosemide was substituted. The water solubility of furosemide was found to be 0.06%.

EXAMPLE 2

Example 1 was repeated and 3.5 grams of the dry complexed product were dissolved in 5.0 grams of distilled water. The resulting solution was adjusted to a pH of 6.2 with concentrated hydrochloric acid. This aqueous solution, containing 10.5% of chlorothiazide and furosemide, remained clear and its clarity did not diminish after standing for 1 week.

EXAMPLE 3

COMPARATIVE EXAMPLE

Poly(N-vinyl-2-pyrrolidone K-30 (12.5 grams) was dissolved in 112.5 grams of 0.2% aqueous sodium hydroxide solution. Chlorzoxazone (2.5 grams) was dissolved in 22.5 grams of 2% sodium hydroxide solution.

The solutions were mixed and coprecipitated using the procedure of Example 1. Two grams of the resulting solid were placed in a screwcap jar and 20 grams of distilled water were added. After shaking for 1 hour, the solution was acidified to pH 5.5 with concentrated hydrochloric acid. The solid precipitated out of the solution, and remained insoluble even when it was diluted further with the addition of another 20 grams of distilled water and shaken overnight.

Examples 1 and 2 are intended to set forth preferred embodiments of the present invention; however, many variations and modifications of the above experiment and complexed products will become apparent from the foregoing description and disclosure. For example, other alkali metal hydroxide solvents, as well as other higher or lower molecular weight poly(N-vinylpyrrolidones) or other mole ratios of polymer to drug species can be employed to provide the corresponding complexes wherein the water solubility of chlorothiazide and furosemide is markedly increased.

What is claimed is:

1. The water soluble chlorothiazide-furosemide-poly(N-vinyl-2-pyrrolidone) homopolymer complex.

2. The complexed product of claim 1 wherein the complexed product contains between about 8 and about 30 weight % of chlorothiazide plus furosemide with respect to the complexed compound.

3. The complexed product of claim 2 wherein the weight ratio of chlorothiazide to furosemide is between about 1:99 and about 99:1.

4. The complexed product of claim 2 wherein the complexed product contains between about 12 and about 20 weight % of chlorothiazide plus furosemide with respect to the complexed compound and wherein the weight ratio of chlorothiazide to furosemide is between about 45:55 and about 60:40.

5. The complexed product of claim 2 wherein the poly(N-vinyl-2-pyrrolidone) has a K value of from 6 to 90.

6. The complexed product of claim 2 wherein the poly(N-vinyl-2-pyrrolidone) has a K value of from 12 to 30.

7. The complexed product of claim 2 which contains repeating units of complexed furosemide-vinyl pyrrolidone moieties and repeating units of complexed chlorothiazide-vinyl pyrrolidone moieties.

* * * * *